United States Patent [19]

Robertson et al.

[11] Patent Number: 5,250,572
[45] Date of Patent: Oct. 5, 1993

[54] (R)-NORFLUOXETINE IN METHOD FOR OCCUPYING SEROTONIN IC RECEPTORS

[75] Inventors: David W. Robertson, San Diego, Calif.; David T. Wong, Indianapolis, Ind.

[73] Assignee: Eli Lilly and Company, Indianapolis, Ind.

[21] Appl. No.: 873,521

[22] Filed: Apr. 21, 1992

Related U.S. Application Data

[63] Continuation of Ser. No. 501,063, Mar. 29, 1990, abandoned.

[51] Int. Cl.$^5$ ............................................ A61K 31/165
[52] U.S. Cl. ..................... 514/651; 514/811; 514/813; 514/909; 514/910; 564/304; 564/347
[58] Field of Search ............... 564/304, 347; 514/651, 514/811, 813, 909, 910

[56] References Cited

U.S. PATENT DOCUMENTS

| | | | |
|---|---|---|---|
| 4,018,895 | 4/1977 | Molloy et al. | 564/304 X |
| 4,194,009 | 5/1980 | Molloy et al. | 424/330 |
| 4,313,896 | 2/1982 | Molloy et al. | 260/501.18 |
| 4,314,081 | 2/1982 | Molloy et al. | 564/347 |
| 4,584,404 | 4/1986 | Molloy et al. | 564/347 |
| 4,626,549 | 12/1986 | Molloy et al. | 514/651 |

OTHER PUBLICATIONS

Robertson et al., *J. Med. Chem.*, 31, 1412 (1988).
Wong et al., *Drug Development Research*, 6, 397 (1985).
Fuller et al., *Pharmacology Biochemistry and Behavior*, 24, 281 (1986).
Nash et al., *Clin. Chem.*, 28(10), 2100 (1982).
Aronoff et al., *Clin. Pharmacol. Ther.*, 36(1), 138 (1984).
Wong, et al., *Biochemical Pharmacology*, 32(7), 1287 (1983).
Hall, et al., *Acta pharmacol. et toxicol.*, 54, 379 (1984).
Thomas, et al., *Psychopharmacology*, 93, 193 (1987).

*Primary Examiner*—Richard L. Raymond
*Attorney, Agent, or Firm*—Joseph A. Jones; Leroy Whitaker; Robert A. Conrad

[57] ABSTRACT

The present invention provides (R)-norfluoxetine and pharmaceutically acceptable salts thereof capable of selectively occupying 5HT$_{1c}$ receptors.

3 Claims, No Drawings

(R)-NORFLUOXETINE IN METHOD FOR OCCUPYING SEROTONIN IC RECEPTORS

This application is a continuation of application Ser. No. 07/501,063, filed on Mar. 29, 1990, now abandoned.

BACKGROUND OF THE INVENTION

During the past decade, the relationship between monoamine uptake and a variety of diseases and conditions has been appreciated and investigated. For example, the hydrochloride salt of fluoxetine (dl-N-methyl-3-[4-(trifluoromethyl)phenoxy]-3-phenylpropylamine) is a selective serotonin (5-hydroxytryptamine, 5HT) uptake inhibitor. Fluoxetine hydrochloride is marketed under the trademark PROZAC ® for the treatment of depression. This compound is among many taught in U.S. Pat. Nos. 4,018,895, 4,194,009, and 4,314,081 as being potent, selective blockers of serotonin uptake.

Fluoxetine is a racemate of the two enantiomeric forms. The biological and pharmacological activity of each enantiomer has been found to be essentially the same; see, Robertson et al., *J. Med. Chem.*, 31, 1412 (1988) and references cited therein.

Norfluoxetine [3-(4-trifluoromethylphenoxy)-3-phenylpropylamine] is a metabolite of fluoxetine and is known to block monoamine uptake, especially serotonin. See U.S. Pat. No. 4,313,896. Since it is a metabolite of fluoxetine, it is believed that this compound contributes in part to the biological activity seen upon chronic administration of fluoxetine.

In copending application Ser. No. 07/486,478, filed Feb. 28, 1990, now abandoned, it was observed that (S)-norfluoxetine is substantially more active than its (R)-antipode as a serotonin uptake inhibitor. We have now discovered that the (R)-enantiomer of norfluoxetine is a selective agonist of $5HT_{1C}$ receptors.

SUMMARY OF THE INVENTION

This invention provides the compound (R)-norfluoxetine and pharmaceutically acceptable salts and solvates thereof. Also provided is a method for selectively occupying the $5HT_{1C}$ receptor in mammals which comprises administering to a mammal requiring such agonism an effective amount of (R)-norfluoxetine or a pharmaceutically acceptable salt or solvate thereof. Further provided by this invention are pharmaceutical formulations comprising (R)-norfluoxetine, or a pharmaceutically acceptable salt or solvate thereof, in combination with one or more pharmaceutically acceptable carriers, diluents, or excipients therefor.

DETAILED DESCRIPTION AND PREFERRED EMBODIMENT

This invention includes the pharmaceutically acceptable acid addition salts of (R)-norfluoxetine. Since (R)-norfluoxetine is an amine, it is basic in nature and accordingly reacts with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogen phosphate, dihydrogen phosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, propanesulfonates, naphthalene-1-sulfonate, naphthalene-2-sulfonate, mandelate, hippurate, gluconate, lactobionate, and the like salts. Preferred pharmaceutically acceptable acid addition salts include those formed with mineral acids such as hydrochloric acid and hydrobromic acid, and those formed with organic acids such as fumaric acid and maleic acid.

The pharmaceutically acceptable acid addition salts of (R)-norfluoxetine can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

(R)-Norfluoxetine can be prepared by any of a number of methods generally known in the art. For example, there are several methods provided in the literature for making the racemate of norfluoxetine, see U.S. Pat. No. 4,313,896. The racemate of norfluoxetine in turn can be resolved into its (S) and (R) components by standard methods. In particular, norfluoxetine can be reacted with an enantiomerically pure chiral derivatizing agent, resolved on the basis of the different physicochemical properties of the diastereomeric derivatives, and then converted to the two separate enantiomers of norfluoxetine. One particularly preferred method of accomplishing this derivatization is analogous to that described in Robertson et al., *J. Med. Chem.*, 31, 1412 (1988), wherein fluoxetine was reacted with an optically active form of 1-(1-naphthyl)ethyl isocyanate to form a urea derivative of fluoxetine. A similar mixture of norfluoxetine diastereomeric ureas can be separated through high pressure liquid chromatography into the individual diastereomers. Each individual diastereomer, in turn, can then be hydrolyzed to the individual enantiomers of norfluoxetine.

A preferred method of preparing (R)-norfluoxetine is similar to that labeled Scheme I in the Robertson et al. reference. (R)-(-)-3-Chloro-1-phenylpropanol (II) is either commercially available or can be prepared by chiral reduction of 3-chloropropiophenone. II can be transformed into (R)-3-amino-1-phenylpropanol (III). Although a number of routes to convert the chloride intermediate to the amino compound are available, the preferred method is the transformation of the chloride to an intermediate N-substituted phthalimide which can be transformed to the desired primary amino intermediate III. This reaction sequence is a Gabriel synthesis wherein the potassium salt of phthalimide is reacted with (R)-(-)-3-chloro-1-phenylpropanol, preferably in the presence of a nonreactive solvent such as dimethylformamide or especially dimethylsulfoxide, to prepare the (R)-3-phthalimido-1-phenylpropanol intermediate. The phthalimido intermediate may be hydrolyzed to provide the desired amino intermediate III. However, to prevent the possible racemization of the intermediate, the phthalimide intermediate is preferably treated with hydrazine in a nonreactive solvent such as ethanol to provide the desired (R)-3-amino-1-phenylpropanol intermediate III. This latter compound can then be reacted with sodium hydride in dimethylacetamide or some other nonreactive solvent, preferably dimethylsulfoxide, to generate the alkoxide which, upon treatment with 4-chloro-or 4-fluoro-benzotrifluoride, leads to a facile nucleophilic aromatic substitution to provide (R)-norfluoxetine.

Alternatively, commercially available (S)-3-phenyloxiranemethanol ((2S,3S)-(-)-3-phenylglycidol) can be treated with a reducing agent such as sodium bis(2-methoxyethoxy)aluminum hydride in a non-reactive solvent such as dimethoxyethane to provide (R)-1-phenyl-1,3-propanediol. The primary alcohol group of this diol intermediate is then converted into a suitable leaving group which can be displaced with ammonia. For example (R)-1-phenyl-1,3-propanediol is treated with a nonreactive base in an inert solvent, such as the use of triethylamine in tetrahydrofuran or dichloromethane. Treatment with a sulfonyl chloride, such as methanesulfonyl chloride, p-toluenesulfonyl chloride, p-chlorophenylsulfonyl chloride, or preferably p-bromophenylsulfonyl chloride, provides the corresponding sulfonate ester (eg, the mesylate, tosylate, p-chlorophenylsulfonate, or p-bromophenylsulfonate, respectively). When any of these sulfonate esters are treated with ammonia, for example, gaseous ammonia dissolved in an alcohol, such as methanol, under pressure, for example at 60 p.s.i., provides the corresponding amine sulfonate salt which can be converted to III upon treatment with base. This sequence is preferred for large scale preparation.

A less direct way of preparing III involves taking a sulfonate ester (as described in the preceding paragraph) of commercially available (S)-1-phenyl-1,2-ethanediol, protecting the remaining alcohol with, for example, a silyl group, such as reacting the alcohol with t-butyldimethylsilyl chloride in the presence of a non-reactive base, such as imidazole, in an inert solvent such as dimethylformamide. This protected sulfonate ester can then be reacted with cyanide, such as with potassium or sodium cyanide, in a non-reactive solvent, such as dimethylformamide or dimethylsulfoxide, at temperature of about 50°-100° C., to give silyl protected (S)-3-phenyl-3-hydroxypropionitrile, which can be reduced (eg, a borane or aluminum hydride reagent, particularly borane-tetrahydrofuran complex in tetrahydrofuran) and hydrolyzed (eg, treatment with 3 N hydrochloric acid) to give III. This procedure is particularly useful for preparing radiolabelled III, such as by using $^{14}C$-labelled sodium cyanide.

The pharmaceutically acceptable acid addition salts of the invention are typically formed by reacting (R)-norfluoxetine with an equimolar or excess amount of acid. The reactants are generally combined in a mutual solvent such as diethyl ether or benzene, and the salt normally precipitates out of solution within about one minute to 10 days, and can be isolated by filtration.

The following example further illustrates the compound of the present invention and methods for its preparation. The example is not intended to be limiting to the scope of the invention in any respect and should not be so construed.

EXAMPLE 1

(R)-Norfluoxetine

A. Preparation of (R)-3-phthalimido-1-phenylpropanol.

To a solution of 10.09 g of (R)-(+)-3-chloro-1-phenylpropanol in 80 ml of dimethylformamide were added 13.14 g of potassium phthalimide in 80 ml of dimethylformamide. The mixture was heated at 100° C. for 8 hours, allowed to cool to room temperature, and filtered. The filtrate was diluted with water, and the solution extracted 3 times with ethyl acetate. The combined organic extracts were washed once with water, once with 0.2 N sodium hydroxide, once again with water, and once with a saturated solution of sodium chloride, dried over sodium sulfate, and concentrated in vacuo to provide an opaque oil that solidified. Crystallization from ethyl acetate/hexanes provided 11.09 g of the title intermediate as clear pale yellow needles, m.p. 81°-83° C.

Analysis for $C_{17}H_{15}NO_3$: Calc.: C, 72.58; H, 5.38; N, 4.98; Found: C, 72.79; H, 5.29; N, 4.93.

B. Preparation of (R)-3-amino-1-phenyl-1-propanol.

To a solution of 8.0 g of (R)-3-phthalimido-1-phenyl-1-propanol in 200 ml of ethanol was added 4.96 ml of anhydrous hydrazine. The mixture was heated to reflux under a nitrogen atmosphere for 3.5 hours, cooled to room temperature, filtered, and the filtrate concentrated in vacuo. The resulting oil was treated with diethyl ether and 30 ml of 5 N sodium hydroxide. The layers were separated, the aqueous layer extracted with diethyl ether, and the combined organic layers were dried over sodium sulfate and concentrated in vacuo to provide 4 g of a yellow oil. A portion (396 mg) of this oil was treated with oxalic acid in ethyl acetate and crystallized from ethyl acetate/methanol to provide 505 mg of the title intermediate as the oxalate salt, m.p. 163°-165° C.

Analysis of the oxalate salt: $C_{11}H_{15}NO_5$: Calc.: C, 54.77; H, 6.27; N, 5.81; Found: C, 55.01; H, 6.41; N, 5.66.

C. Preparation of (R)-norfluoxetine.

To a slurry of 1.0 g of 60% sodium hydride in oil in 10 ml of dimethylformamide were added 3.6 g of (R)-3-amino-1-phenyl-1-propanol in 50 ml of dimethylformamide. The mixture was heated at 70° C. for 5 minutes. 4-Fluorobenzotrifluoride (3.2 ml) was added to the reaction mixture and the solution heated at 100° C. for 3 hours. The mixture was poured into ice water and extracted three times with diethyl ether. The combined organic extracts were washed twice with water, once with a saturated sodium chloride solution, dried over sodium sulfate and concentrated in vacuo to provide 6.23 g of a yellow oil. The oil was purified by high pressure liquid chromatography over silica gel eluting with a gradient of methylene chloride to 7.5% methanol in methylene chloride to which 0.5% of ammonium hydroxide had been added. The desired fractions were combined and concentrated in vacuo to yield 3.26 g of the title product as a yellow oil. The residue (3.08 g) was dissolved in ethyl acetate and a solution of 1.27 g of maleic acid in ethyl acetate was added. Diethyl ether and hexanes were added and the resulting precipitate was recovered by filtration providing 3.55 g of the desired title product as the maleate salt, m.p. 95°-97° C.

Analysis for $C_{20}H_{20}F_3NO_5$ ((R)-norfluoxetine maleate): Calc.: C, 58.39; H, 4.90; N, 3.41; Found: C, 58.51; H, 4.86; N, 3.41.

According to the same procedure described above beginning with (S)-(-)-3-chloro-1-phenyl-1-propanol, (S)-norfluoxetine was prepared. The maleate salt (hemihydrate) of (S)-norfluoxetine had a melting point of 94°–96° C.

(R)-Norfluoxetine is useful as an agonist of 5HT$_{1C}$ receptors. Therefore, another embodiment of the present invention is a method for occupying 5HT$_{1C}$ receptors in mammals which comprises administering to a mammal requiring such agonism a pharmaceutically effective amount of (R)-norfluoxetine or a pharmaceutically acceptable salt thereof.

The term "pharmaceutically effective amount", as used herein, represents an amount of (R)-norfluoxetine which is capable of occupying 5HT$_{1C}$ receptors. The particular dose of compound administered according to this invention will, of course, be determined by the particular circumstances surrounding the case, including the route of administration, the particular condition being treated, and similar considerations. (R)-Norfluoxetine can be administered by a variety of routes including the oral, rectal, transdermal, subcutaneous, intravenous, intramuscular or intranasal routes. A typical daily dose will contain from about 0.01 mg/kg to about 20 mg/kg of (R)-norfluoxetine. Preferred daily doses will be about 0.05 to about 10 mg/kg, ideally about 0.1 to about 5 mg/kg.

(R)-Norfluoxetine has the ability to treat a variety of disorders in mammals associated with dysfunction in serotonergic systems involving the 1C receptor such as obesity, bulimia, alcoholism, pain, sleep apnea, substance abuse (eg, cocaine, heroin, amphetamines, etc.), obsessive-compulsive disorders, and migraine. (R)-Norfluoxetine also has little effect on metabolism of concurrently administered drugs such as barbiturates or tricyclic antidepressants, unlike fluoxetine. (R)-Norfluoxetine is relatively non-toxic and has an excellent therapeutic index. Moreover, this compound is surprisingly selective as a 5HT$_{1C}$ receptor agonist. Therefore, the present invention also provides methods of treating the above disorders at rates set forth above for occupying 5HT$_{1C}$ receptors in mammals.

The following experiment was conducted to demonstrate the ability of (R)-norfluoxetine to affect radioligand binding to five subtypes of serotonin receptors. This general procedure is set forth by Wong et al., *Life Sciences*, 46, 231 (1990).

Bovine choroid plexus and brain tissues from male Sprague-Dawley rats was homogenized in 9 volumes of 0.32 M sucrose. After centrifugation at 1000×g for 10 minutes and then at 17,000×g for 20 minutes, a crude synaptosomal fraction was sedimented. The pellet was suspended in 100 volumes of 50 mM Tris-HCl, pH 7.4, incubated at 37° C. for 10 minutes, and centrifuged at 50,000×g for 10 minutes. The process was repeated, and the final pellet of membrane was suspended in ice-chilled 50 mM Tris-HCl buffer, pH 7.4.

Binding of $^3$H-mesulergine to the 5HT$_{1C}$ receptor and other serotonergic $^3$H-ligands to subtypes of 5HT receptors ($^3$H-8-hydroxy-2-(di-n-propylamino)tetralin to 5HT$_{1A}$; $^3$H-serotonin to 5HT$_{1B}$ and 5HT$_{1D}$; $^3$H-ketanserin to 5HT$_2$; and $^3$H-1-methyl-N-(8-methyl-8-azabicyclo[3.2.1]oct-3-yl)-1H-indazaole-3-carboxamide to 5HT$_3$ receptors) was performed according to the method described in the above reference. Briefly, membranes isolated from bovine choroid plexus (for 5HT$_{1C}$) or rat brain were incubated at 25° C. for 30 minutes in 2 ml of 50 mM Tris-HCl, pH 7.4; 10 mM pargyline, 0.6 mM ascorbic acid; 5 mM CaCl$_2$; and 2 nM $^3$H-mesulergine or other tritiated ligand. Binding was terminated by filtering samples under reduced pressure through glass fiber (GFB) filters. The filters were washed 3 times with 5 ml of ice cold buffer and placed in scintillation vials with 10 ml of PCS (Amersham/Searle) scintillation fluid. Radioactivity was measured with a liquid scintillation spectrometer. Serotonin at 10 μM also included in separate samples to determine specific binding, which accounted for 90–70 percent of total binding.

The results of the evaluation of (R)-norfluoxetine from these experiments are set forth below in Table I. In the Table, columns 2–6 provide the micromolar (μM) concentration of the test compound needed to inhibit radioligand binding by 50% for each of the indicated receptors.

TABLE I

| AFFINITIES OF (R)-NORFLUOXETINE FOR SUBTYPES OF SEROTONIN RECEPTORS | | | | | | |
|---|---|---|---|---|---|---|
| | Inhibition of Radioligand Binding to 5HT Receptor* | | | | | |
| Compound | 1A | 1B | 1C** | 1D | 2 | 3 |
| (R)-Norfluoxetine | 22 | 24 | 0.47 | 101 | 7.9 | 12 |

*IC50 in μM (MICROMOLAR OR 10$^{-6}$ M)
**Mean of three experiments

The compound and salts of the present invention are preferably formulated prior to administration. Therefore, yet another embodiment of the present invention is a pharmaceutical formulation comprising (R)-norfluoxetine, or a pharmaceutically acceptable salt thereof, and one or more pharmaceutically acceptable carriers, diluents or excipients therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl-and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 100 mg, more usually about 20 to about 80 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| (R)-Norfluoxetine hydrochloride | 20 |
| starch, dried | 200 |
| magnesium stearate | 10 |
| Total | 230 mg |

The above ingredients are mixed and filled into hard gelatin capsules in 230 mg quantities.

Formulation 2

A tablet is prepared using the ingredients below:

|  | Quantity (mg/tablet) |
| --- | --- |
| (R)-Norfluoxetine hydrochloride | 50 |
| cellulose, microcrystalline | 400 |
| silicon dioxide, fumed | 10 |
| stearic acid | 5 |
| Total | 465 mg |

The components are blended and compressed to form tablets each weighing 465 mg.

Formulation 3

An aerosol solution is prepared containing the following components:

|  | Weight % |
| --- | --- |
| (R)-Norfluoxetine oxalate | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are than fitted to the container.

Formulation 4

Tablets each containing 60 mg of active ingredient are made as follows:

| (R)-Norfluoxetine phosphate | 60 mg |
| --- | --- |
| starch | 45 mg |
| microcrystalline cellulose | 35 mg |
| polyvinylpyrrolidone | 4 mg |
| (as 10% solution in water) sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| (R)-Norfluoxetine tartrate | 80 mg |
| --- | --- |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| (R)-Norfluoxetine | 225 mg |
| --- | --- |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| (R)-Norfluoxetine napsylate | 50 mg |
| --- | --- |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| (R)-norfluoxetine hydrochloride | 100 mg |
|---|---|
| isotonic saline | 1000 ml |

The solution of the above ingredients is administered intravenously at a rate of 1 ml per minute to a subject suffering from depression.

We claim:

1. A method for occupying serotonin 1C receptors in mammals which comprises administering to a mammal requiring altered neurotransmission of serotonin an effective amount of (R)-norfluoxetine or a pharmaceutically acceptable acid addition salt or solvate thereof, substantially free of (S)-norfluoxetine.

2. The method of claim 1 employing (R)-norfluoxetine.

3. The method of claim 1 employing (R)-norfluoxetine hydrochloride.

* * * * *